United States Patent
Peyman

(10) Patent No.: US 6,551,307 B2
(45) Date of Patent: Apr. 22, 2003

(54) VISION CORRECTION USING INTRASTROMAL POCKET AND FLAP

(76) Inventor: Gholam A. Peyman, 8654 Pontchartrain Blvd., Unit #1, New Orleans, LA (US) 70124

(*) Notice: Subject to any disclaimer, the term of this patent is extended or adjusted under 35 U.S.C. 154(b) by 0 days.

(21) Appl. No.: 09/843,141

(22) Filed: Apr. 27, 2001

(65) Prior Publication Data

US 2002/0138070 A1 Sep. 26, 2002

Related U.S. Application Data

(63) Continuation-in-part of application No. 09/815,277, filed on Mar. 23, 2001.

(51) Int. Cl.[7] .................................................. A61F 9/007
(52) U.S. Cl. ............................ 606/5; 606/10; 128/898
(58) Field of Search .............................. 128/898; 606/5, 606/10; 607/88

(56) References Cited

U.S. PATENT DOCUMENTS

| | | |
|---|---|---|
| 3,982,541 A | 9/1976 | L'Esperance, Jr. |
| 4,298,004 A | 11/1981 | Schachar et al. |
| 4,452,235 A | 6/1984 | Reynolds |
| 4,655,774 A | 4/1987 | Choyce |
| 4,665,913 A | 5/1987 | L'Esperance, Jr. |
| 4,669,466 A | 6/1987 | L'Esperance |
| 4,676,790 A | 6/1987 | Kern |
| 4,718,418 A | 1/1988 | L'Esperance, Jr. |
| 4,729,372 A | 3/1988 | L'Esperance, Jr. |
| 4,744,360 A | 5/1988 | Bath |
| 4,807,623 A | 2/1989 | Luberman |
| 4,840,175 A | 6/1989 | Peyman |
| 4,903,695 A | 2/1990 | Warner et al. |
| 4,907,586 A * | 3/1990 | Bille et al. .................... 606/5 |
| 4,961,744 A | 10/1990 | Kilmer et al. |
| 4,994,058 A | 2/1991 | Raven et al. |
| 5,063,942 A | 11/1991 | Kilmer et al. |
| 5,196,026 A | 3/1993 | Barrett et al. |
| 5,196,027 A | 3/1993 | Thompson et al. |
| 5,215,104 A | 6/1993 | Steinert |
| 5,300,118 A | 4/1994 | Silvestrini et al. |
| 5,318,044 A | 6/1994 | Kilmer et al. |
| 5,318,047 A | 6/1994 | Davenport et al. |
| 5,323,788 A | 6/1994 | Silvestrini et al. |
| 5,336,261 A | 8/1994 | Barrett et al. |
| 5,368,604 A | 11/1994 | Kilmer et al. |
| 5,391,201 A | 2/1995 | Barrett et al. |
| 5,403,335 A | 4/1995 | Loomas et al. |
| 5,405,384 A | 4/1995 | Silvestrini |
| 5,720,894 A | 2/1998 | Neev et al. |
| 5,722,971 A | 3/1998 | Peyman |
| 5,919,185 A | 7/1999 | Peyman |
| 6,086,204 A | 7/2000 | Magnante |
| 6,102,946 A | 8/2000 | Nigam |
| 6,264,648 B1 | 9/2001 | Peyman |
| 6,376,153 B2 * | 11/2001 | Goodman et al. ............ 607/88 |

OTHER PUBLICATIONS

L. Girard, "Corneal Surgery", The C.V. Mosby Publishing Company, London 1981 pp. 107–141.

Tadeusz Krwawicz, "Lamellar Corneal Stromectomy for the Operative Treatment of Myopia", Notes, Cases, Instruments, pp. 828–833.

(List continued on next page.)

Primary Examiner—David M. Shay

(57) ABSTRACT

A method of modifying a cornea of an eye, including the steps of separating an internal portion of the cornea into first and second internal corneal surfaces. Ocular material is then inserted in-between the first and second corneal surfaces. A flap is formed on the surface of the cornea and moved to expose a third internal corneal surface, which is ablated with a laser.

36 Claims, 7 Drawing Sheets

OTHER PUBLICATIONS

Barraquer, "Keratomileusis and Keratophakia in the Surgical Correction of Aphakia", Cataract Surgery and Special Techniques prior to 1996, pp. 270–289.

Baumgartner et al., "Refractive Keratoplasty: Acute Morphologic Features," the CLAO Journal—Apr., 1985, vol. II, No. 2, pp 163–169.

Werblin, "Epikeratophakia: Techniques, Complications and Clinical Results", Ophthalmology, prior to 1996, pp. 45–58.

Sally Pobojewski, "New U–developed laser performs high–precision corneal surgery", News and Information Services, The University Record, Jul. 16, 1997.

Karin R. Sletten, MD et al.; Experimental Science, "An In Vivo Model of Femtosecond Laser Intrastromal Refractive Surgery", Ophthalmic Surgery and Lasers, Nov./Dec. 1999, vol. 30, No. 9, pp. 742–749.

Griffith et al.; "Functional Human Corneal Equivalents Constructed from Cell Lines", Science, vol. 286, Dec. 10, 1999 pp. 2169–2172.

Yamauchi et al.; "Cultivation of fibroblast cells on keratin-–coated substrata", Polymers for Tissue Engineering, pp. 329–340, VS 1998.

Ijima et al.; "Formation of a spherical multicellular aggregate (spheroid) of animal cells in the pores of polyurethane foam as a cell culture substratum and its application to a hybrid artificial liver", Polymers for Tissue Engineering, pp. 273–286, VSP 1998.

Cao et al.; "Comparative study of the use of poly(glycolic acid), calcium alginate and pluronics in the engineering of autologous procine cartilage", Polymers for Tissue Engineering, pp. 316–327, VSP 1998.

Binder et al.; "Hydrogel keratophakia in non–human primates", Current Eye Research, vol. 1, No. 9, 1981/1982, pp. 535–542.

Swinger et al.; "Keratophakia and Keratomileusis—Clinical Results", American Academy of Opthalmology, Aug. 1981, vol. 88, No. 8, pp. 709–715.

* cited by examiner

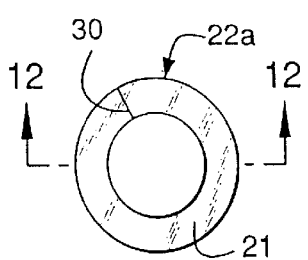
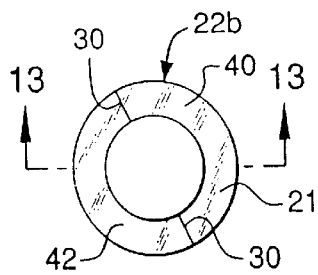
FIG. 9　　　　　　　　FIG. 10
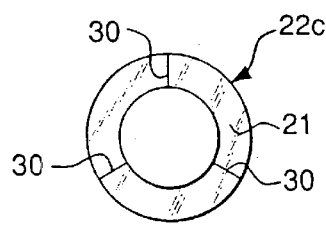
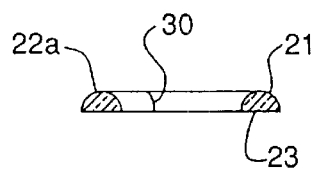
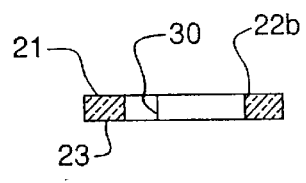
FIG. 11　　　　FIG. 12　　　　FIG. 13
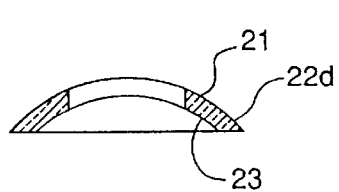
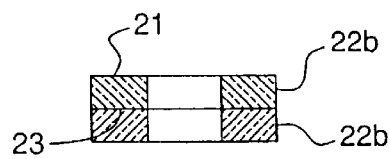
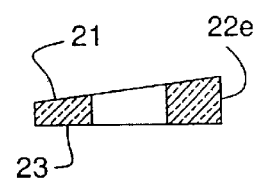
FIG. 14　　　　FIG. 15　　　　FIG. 16
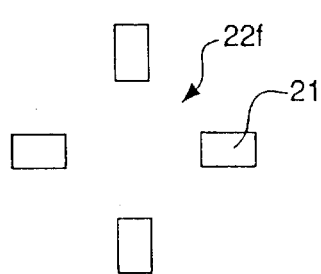
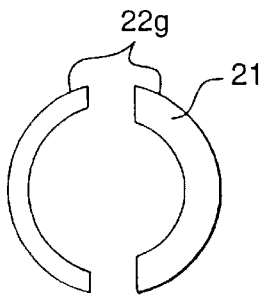
FIG. 17　　　　FIG. 18

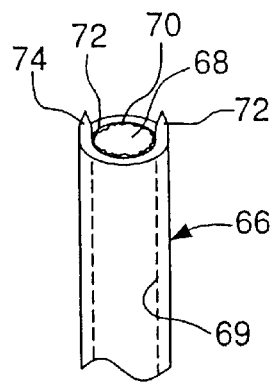
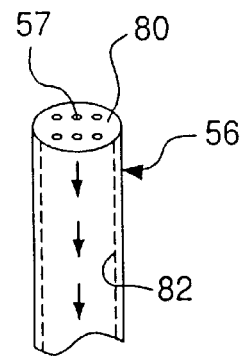
FIG. 29  FIG. 30
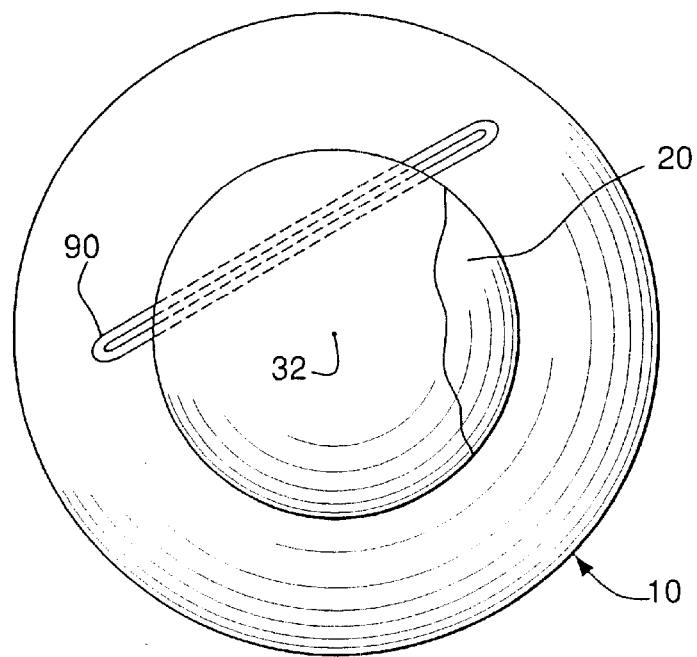
FIG. 31

VISION CORRECTION USING INTRASTROMAL POCKET AND FLAP

RELATED APPLICATIONS

This application is a continuation-in-part of U.S. patent application Ser. No. 09/815,277, filed Mar. 23, 2001, the entire contents of which are herein incorporated by reference.

Additionally, this application is related to U.S. application Ser. No. 09/758,263, filed Jan. 12, 2001, the entire contents of which are herein incorporated by reference.

FIELD OF THE INVENTION

The present invention relates to a method for modifying a live cornea to correct refractive error. In particular, the live cornea is modified by using a laser to separate an internal area of the live cornea into first and second opposed internal surfaces, which define a pocket therebetween. An ocular material is then introduced into the pocket, which changes the shape of the cornea. Additionally, a flap can be formed in the surface of the cornea. The flap can be moved to expose an internal surface of the cornea, which is ablated to further correct the refractive error of the cornea.

BACKGROUND OF THE INVENTION

A conventional method for correcting the refractive error in a cornea is keratophakia, i.e., implantation of a lens inside the cornea. Keratophakia uses an implant which is placed into the cornea approximately equidistant from the exterior surface of the cornea and the interior surface. The procedure is usually done by first preparing a lens from corneal donor tissue or synthetic material using a cryo-lathe. The lens is implanted by removing a portion of the cornea with a device called a microkeratome, and the tissue is sutured back into place over the lens. However, there can be problems when microkeratomies are used for cutting the cornea. First, irregular keratectomies or perforations of the eye can result. Second, the recovery of vision can be rather prolonged.

Another surgical technique exists that uses a femtosecond laser to separate layers inside the stromal, at least two-thirds of the distance from the top surface of the cornea to the inside of the eye. An incision is made to access this area and a solid inlay is inserted to help correct myopia in the eye. By separating the layers in the bottom two-thirds of the stromal, it is difficult to access the separated area to insert the inlay and virtually impossible to change or modify the inlay without another extensive surgical procedure. This procedure requires making an incision which is parallel to the visual axis and is limited in the lateral direction by a maximum size of 0.3 mm to encase a relatively rigid inlay that forces the tissue in the lateral direction.

Additional surgical techniques exist that use ultraviolet light and short wavelength lasers to modify the shape of the cornea. For example, excimer lasers, such as those described in U.S. Pat. No. 4,840,175 to Peyman, which emit pulsed ultraviolet radiation, can be used to decompose or photoablate tissue in the live cornea so as to reshape the cornea.

Specifically, the Peyman patent discloses the laser surgical technique known as laser in situ keratomycosis (LASIK). In this technique, a portion of the front of the live cornea can be cut away in the form of a flap having a thickness of about 160 microns. This cut portion is removed from the live cornea to expose an inner surface of the cornea. A laser beam is then directed onto the exposed inner surface to ablate a desired amount of the inner surface up to 150–180 microns deep. The cut portion is reattached over the ablated portion of the cornea and assumes a shape conforming to that of the ablated portion. Additionally, in the Lasik procedure, a femtosecond laser can be used to cut and separate the flap.

However, because only certain amount of cornea can be ablated without the remaining cornea becoming unstable or experiencing outbulging (eklasisa), this technique is not especially effective in correcting very high myopia. That is, a typical cornea is on average about 500 microns thick. The laser ablation technique requires that at least about 250 microns of the corneal stroma remain after the ablation is completed so that instability and outbulging do not occur.

Additional methods for correcting the refractive error in the eye include inserting an implant in-between layers of the cornea. Generally, this is achieved using several different methods. The first method involves inserting a ring between layers of the cornea, as described in U.S. Pat. No. 5,405,384 to Silvestrini. Typically, a dissector is inserted in the cornea and forms a channel therein. Once it is removed, a ring is then inserted into the channel to alter the curvature of the cornea. In the second method, a flap can be created similarly to the LASIK procedure and a lens can be inserted under the flap, as described in U.S. Pat. No. 6,102,946 to Nigam. The third method involves forming a pocket using an instrument, and inserting an implant into the pocket, as described in U.S. Pat. No. 4,655,774 to Choyce.

However, with the above described techniques, a knife or other mechanical instrument is generally used to form the channel, flap or pocket. Use of these instruments may result in damage or imprecision in the cut or formation of the desired area in which the implant is placed.

Therefore, there exists a need for an improved method of correcting refractive error in the cornea of an eye.

SUMMARY OF THE INVENTION

Accordingly, it is an object of the present invention to provide an improved method for modifying the cornea of an eye.

Another object of the present invention is to provide a method for modifying the cornea of an eye that results in a precise separation between layers in the cornea.

Still another object of the present invention is to provide a method for modifying the cornea of an eye that allows for corrective measures that avoid or eliminate outbulging or instability in the cornea.

Yet another object of the present invention is to provide a method for modifying the cornea of an eye that avoids or eliminates most of the risks of damage due to use of knives or other mechanical instruments.

The foregoing objects are basically attained by a method of modifying the cornea of an eye, that includes separating an internal portion of the cornea into first and second internal corneal surfaces. Ocular material is then inserted in-between the first and second corneal surfaces and a flap is formed on the surface of the cornea. The flap is then moved to expose a third internal corneal surface and the third corneal surface is ablated by a laser.

Other objects, advantages, and salient features of the present invention will become apparent to those skilled in the art from the following detailed description, which, taken in conjunction with the annexed drawings, discloses preferred embodiments of the invention.

BRIEF DESCRIPTION OF THE DRAWINGS

Referring to the drawings which form a part of this disclosure:

FIG. 9 is a front elevational view of a split ring ocular implant for use in the procedure shown in FIGS. 1–4 and 19–24;

FIG. 10 is a front elevational view of a two part ocular implant for use in the procedure shown in FIGS. 1–4 and 19–24;

FIG. 11 is a front elevational view of a three part ocular implant for use in the procedure shown in FIGS. 1–4 and 19–24;

FIG. 12 is a side elevational view in cross-section of the ocular implant of FIG. 9, taken along lines 12—12;

FIG. 13 is a side elevational view in cross-section of the ocular implant of FIG. 10, taken along lines 13—13;

FIG. 14 is a side elevational view in cross-section of an arcuate ocular implant for use in the procedure shown in FIGS. 1–4 and 19–24;

FIG. 15 is a side elevational view in cross-section of multiple ocular implants stacked on top of one another for use in the procedure shown in FIGS. 1–4 and 19–24;

FIG. 16 is a side elevational view in cross-section of an ocular implant having a non-uniform thickness for use in the procedure shown in FIGS. 1–4 and 19–24;

FIG. 17 is a front elevational view in cross-section of an ocular implant having four separate portions for use in the procedure shown in FIGS. 1–4 and 19–24;

FIG. 18 is a front elevational view in cross-section of an ocular implant having two portions of different thickness for use in the procedure shown in FIGS. 1–4 and 19–24;

FIG. 29 is a top perspective view of a device for forming the flap of FIGS. 25–28.

FIG. 30 is a top perspective view of a suction device for removing the flap of FIGS. 25–28.

FIG. 31 is a method of forming a flap in the cornea of an eye, by cutting the cornea using a cutting tool.

DETAILED DESCRIPTION OF THE PREFERRED EMBODIMENT

Figure 1:
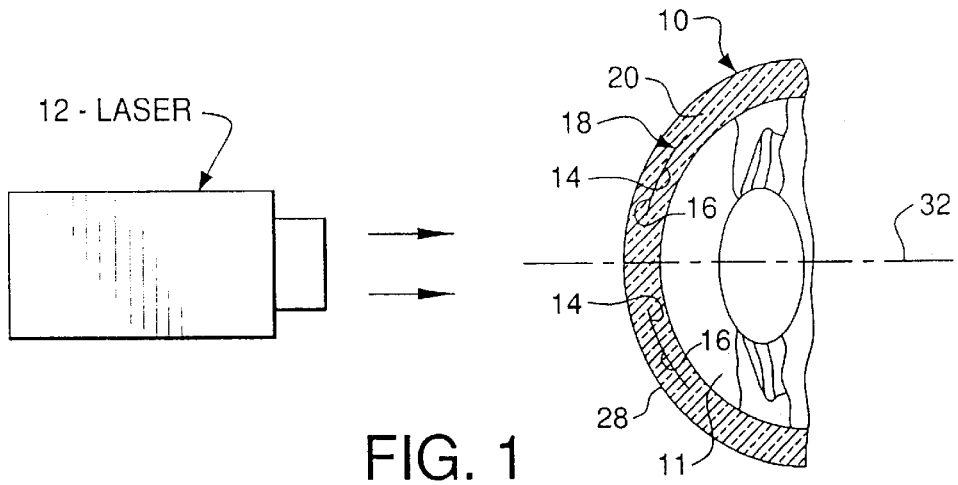
FIG. 1 illustrates a method of forming a pocket in the cornea of an eye, by irradiating the cornea with an ultrashort pulse laser, according to the preferred embodiment of the present invention.
Figure 2:
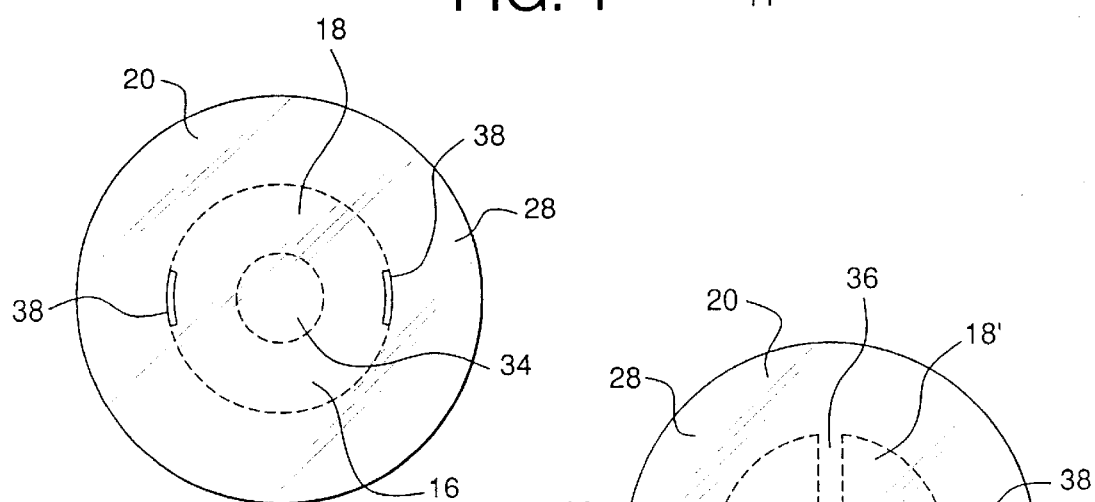
FIG. 2 is an elevational front view of the eye and the pocket of FIG. 1.
Figure 3:
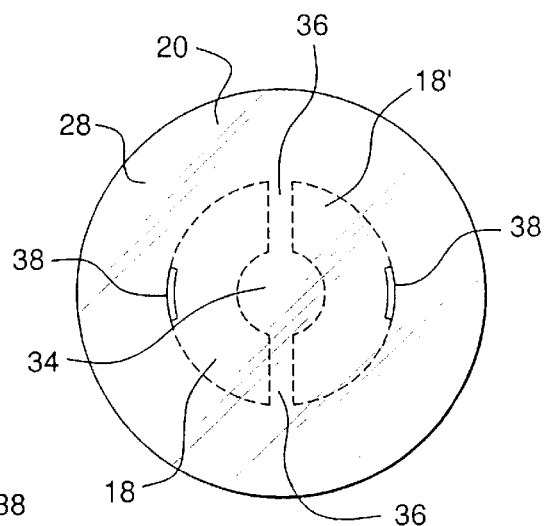
FIG. 3 is an elevational front view of a second embodiment of the invention wherein two pockets are formed by an ultrashort pulse laser.

As initially shown in FIGS. 1, 2 and 19–24, the refractive properties of eye 10 can be altered by using laser 12 to separate an inner portion of the cornea into first internal corneal surface 14 and second internal corneal surface 16, creating internal corneal pocket 18 in the cornea 20 and then placing ocular material or an implant 22 in the pocket 18. Additionally, the cornea can be shaped by using a second laser 24 to ablate a portion 26 of the surface 28 of the cornea 16, or an external lens 29 to mold the ocular material.

To begin, the refractive error in the eye is measured using wavefront technology, as is known to one of ordinary skill in the art. For a more complete description of wavefront technology see U.S. Pat. No. 6,086,204 to Magnate, the entire contents of which is incorporated herein by reference. The refractive error measurements are transmitted to a computerized lathe (not shown) or other lens-shaping machine, where the shape of ocular material is determined using the information from the wavefront device. Alternatively, the ocular material 22 can be manufactured or shaped prior to the use of the wavefront technology and can be stored in a sterilized manner until that specific shape or size is needed.

Ocular material or inlay 22 has a first surface 21 and a second surface 23 and is porous to allow oxygen and nutrients to pass therethrough. Materials that are suitable for these purposes are preferably any polymer or hydrogel having about 50% water content; however, the water content can be any percentage desired. The ocular material may be formed from synthetic or organic material or a combination thereof. For example, the ocular material can be collagen combined with or without cells; a mixture of synthetic material and corneal stromal cells; silicone or silicone mixed with collagen; mucopolysacharide; chodrotin sulfate; elsatins; methylmetacrylate; hydrogel; any transparent material, such as polyprolidine, polyvinylpylidine, polyethylenoxide, etc.; or any deformable and/or porous polymer, which can change its shape with radiation after implantation. The collagen can be a semiliquid, a gel, human or other animal, or it can de derivatized.

Generally, ocular material 22 is preferably about 0.5 mm to 5 mm wide. The thickness is preferably about 5–2000 microns, and more preferably less than 200 microns. The inside edge can be thinner or thicker than the outside edge; for example, the inside edge can have a thickness of about 1–100 microns, while the outside edge has a thickness of about 20–3000 microns. However, the ocular material can have any thickness or configuration that would allow it to elevate or move any portion of surface 14 relative to surface 16. The thickness and position of ocular material 22 generally defines the degree of correction.

Figure 6:
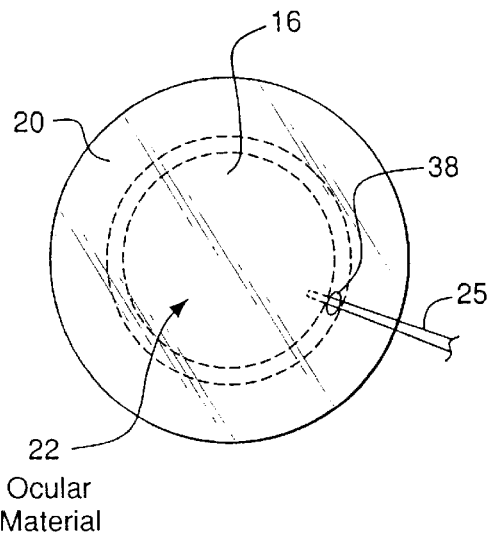
FIG. 6 is an elevational front view of a fifth embodiment of the present invention wherein a needle is used to inject ocular material into a pocket formed by an ultrashort pulse laser.

Preferably, ocular material 22 is a liquid or a gel that can be injected through the surface of the cornea using an injection device 25, such as a needle, without making a large incision or opening in the surface of the lens, as seen in FIG. 6. By injecting a gel into a pocket in this manner, the gel is confined to the corneal pocket 18 and will settle or move in the pocket in a predictable configuration or distribution. In other words, the gel will not flow through the layers of the cornea, but will rather stay inside the structure or confines of the pocket. The gel can be inserted into a pocket that encompasses the entire front of the cornea, or extend past the cornea and Bowman layer to the sclera. By extending the pocket past the Bowman layer, the portion of the cornea above the pocket would become loose. The injection of the gel would allow lifting of the Bowman layer, lifting up the entire front surface of the cornea, allowing the eye to be reshaped as desired. However, the gel can be injected or positioned into any size pocket desired and the pocket does not have to encompass the entire front of the cornea. Additionally, as described below, the ocular material does not necessarily need to be a gel in this process and may be a lens or any other desired material.

Furthermore, the ocular material 22 can include a silicone polymer which includes loose monomers that are responsive to light (both visible and invisible) within a certain wavelength range, such as the short ultraviolet wavelength range or the blue light wavelength range. In response to the light, the monomers become aggravated, and cross-linking occurs which increases the volume of the area of ocular material 22 or a portion of the ocular material, without substantially ablating the ocular material 22, as well as fixing or hardening the ocular material.

The ocular material 22 can also include a polymer comprising a polycarbonate or acrylic material containing a dye or dyes manufactured, for example, by Centex Company. The dye or dyes absorb light within a certain wavelength range, such as the infrared wavelength range, which causes slight melting or reduction of the material or a portion of the ocular material, as well as solidification. This melting or reduction results in a decrease or flattening of the irradiated area of the ocular material 22, and thus reduces the volume of that area for purposes discussed in more detail below, without substantially ablating the ocular material 22.

See also U.S. application Ser. No. 09/532,516, filed Mar. 21, 2000 which is herein incorporated by reference, for a further discussion of swelling or shrinking of ocular material.

Figure 5:
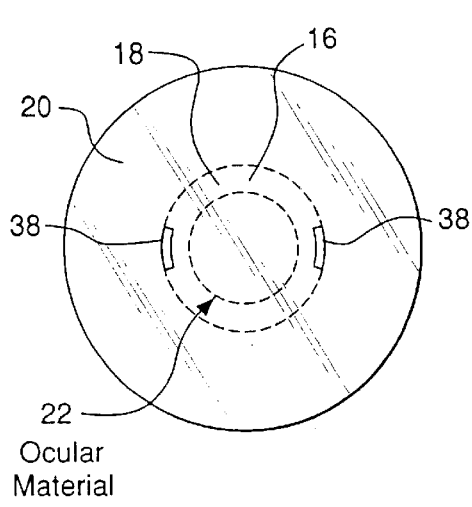
FIG. 5 is an elevational front view of a fourth embodiment of the present invention wherein no central portion is left attached in a pocket formed by the ultrashort pulse laser.

Ocular material 22 can also be a lens. When a lens, it can be any shape or sized desired. As seen in FIGS. 6–15, the lens is preferably substantially ring-shaped; but can be a circular or semicircular inlay. For example, unitary lenses 22a–c have a split 30 or have multiple portions that couple or fit together (FIGS. 9–11), lens 22b is flat (FIG. 13), lens 22d is arcuate (FIG. 14), and lens 22a has tapered edges (FIG. 12). Additionally, ocular material 22 may have any combination of these properties. When the lens has multiple portions, as seen in lenses 22f and 22g, the portions can couple together, simply abut one another, they can lay near each other, not necessarily touching each other or the lens portions can be separated from each other (FIGS. 17 and 18). Lens 22b can have multiple layers on top of each other (FIG. 15), or lens 22c and 22g can have two sides with different thickness (FIGS. 16 and 18), which would help to correct astigmatism. Additionally, the lens preferably allows light in the visible spectrum to pass therethrough and can have different or similar refractive properties to the refractive properties of the cornea, it can have pigmentation added thereto to change the color of the lens or it can be photochromatic. Furthermore, it is not necessary for the lens to have a hole or aperture therethrough. The lens can have a substantially planar surface or an arcuate surface with no holes or apertures therein, as seen specifically in FIG. 5.

Figure 4:
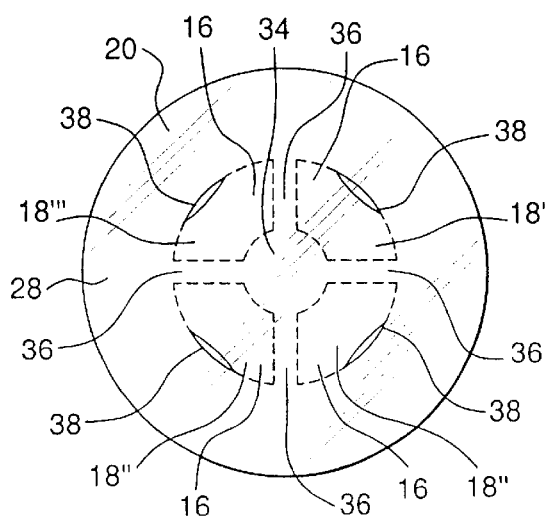
FIG. 4 is an elevational front view of a third embodiment of the present invention wherein four pockets are formed by an ultrashort pulse laser.

As seen specifically in FIGS. 1–5, a laser 12 is aimed at an internal portion of the cornea, adjacent the external surface of the cornea of the eye and fired. Preferably, the laser is focused to create the pocket 18 in the first one-third of the cornea, and not in the back of the cornea. In other words, the pocket is preferably formed adjacent surface 28 or closer to surface 28 then to the interior or anterior chamber 11 of eye 10. By forming the pocket in the first one-third of the cornea, the pocket or pockets may extend beyond the Bowmans layer and the cornea, to create a large pocket, which would allow raising of the entire front portion of the cornea, as described above. The laser preferably separates an internal area of the cornea offset from the main optical or visual axis 32 into first 14 and second 16 substantially ring-shaped internal surfaces to form the circular or ring-shaped corneal pocket 18. First internal corneal surface 14 faces in a posterior direction of cornea 20 and the second internal corneal surface 16 faces in an anterior direction of the cornea 20. The distance from first internal corneal surface 14 to the exterior corneal surface 28 is preferably a uniform thickness of about 10–250 microns, and more preferably about 80–100 microns, but can be any suitable thickness and does not necessarily need to be substantially uniform. A portion 34 of first and second surfaces 14 and 16 preferably remains attached to each other by an area located at the main optical axis 32. However, the laser can form a pocket 18 of any suitable configuration, such as a pocket that is not attached at the main optical axis (FIG. 5), two substantially similar pockets 18 and 18' (FIG. 3) or four pockets 18, 18', 18'' and 18''' (FIG. 4). When multiple pockets are formed, preferably the pockets are separated by a portion 36, which is an area where first and second surfaces 14 and 16 remain attached. However, the pocket or pockets may be any number, shape or size desired and they do not need to be circular or ring-shaped. Furthermore, a flap similar to the above-described pocket, and as described in U.S. patent application Ser. No. 09/758, 263 can be formed using laser 12 or a cutting tool or knife 90 (FIG. 31), such as a microkeratome, or any other device known in the art.

Laser 12 preferably is an ultrashort pulse laser, such as a femto, pico, or attosecond laser; but may be any light emitting device suitable for creating a pocket in the cornea as described above. The ultrashort pulse laser is positioned in front of the eye and is focused at the desired depth in the cornea and in the desired pocket configuration. Ultrashort pulse lasers are desired since they are high precision lasers that require less energy than conventional lasers to cut tissue and do not create "shock waves" that can damage surrounding structures. Cuts made by ultrashort pulse lasers can have very high surface quality with accuracy better than 10 microns, resulting in more precise cuts than those made with mechanical devices or other lasers. This type of accuracy results in less risks and complications than the procedures using other lasers or mechanical devices.

As seen in FIGS. 2–5, an incision or opening 38 is made in the surface 28 of the cornea to access pocket 18 or pockets 18', 18" and 18'". Preferably, the incision 38 is made at the periphery of the pocket; however, it may be made anywhere desired that would allow access to the pocket 18. Additionally, multiple incisions can be made that would allow access to different portions of pocket 18 or different pockets 18', 18" and 18'". A carved instrument (not shown) can be inserted through the incision, which would dissect the pocket, if needed. A carved instrument is generally used to extend the pocket 18 past the cornea or Bowmans layer to the sclera as described above. However, a large incision may not be necessary, as in the case where a gel is inserted using a needle, as described above.

Figure 19:
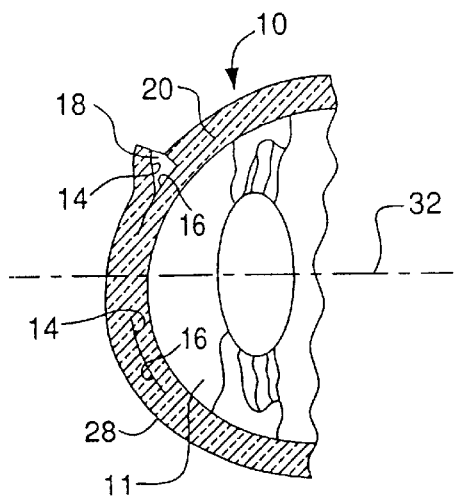
FIG. 19 is a side elevational view in cross section similar to that shown in FIG. 1 with the incision in the pocket open.
Figure 20:
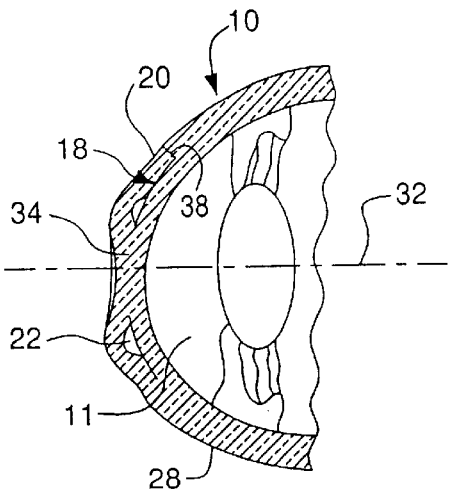
FIG. 20 is a side elevational view in cross section similar to that shown in FIG. 19, except that an annular or circular ocular implant has been introduced through the incision and between the internal surfaces.

As seen in FIGS. 19 and 20, the ocular material 22 is then inserted through the incision 28 or any other opening by opening the incision using any device known in the art, such as spatula or microforceps or any other device. Preferably, when a lens is used, it has at least two separate portions 40 and 42 (FIG. 10) or has a split 30 (FIG. 9) that allow the ocular material 22 to be positioned or introduced around or at least partially encircling the main optical axis 32 or portion 34 and in between the first and second internal surfaces 14 and 16 that define the pocket 18. However, as stated above the first and second surfaces 14 and 16 do not necessarily have to be attached at the main optical axis and in such a case, ocular material 22 is merely placed in pocket 18.

Figure 7:
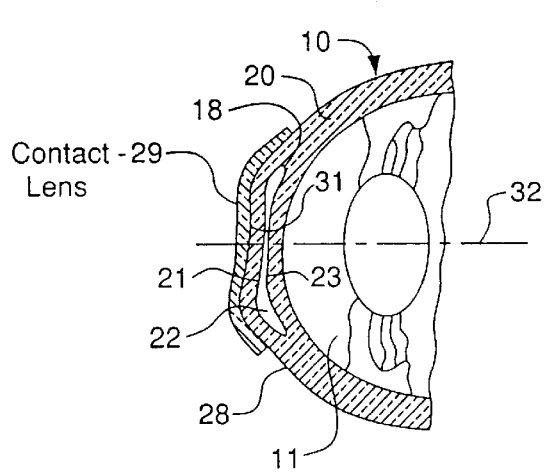
FIG. 7 is a cross-sectional side view of the eye of FIG. 6 with a contact lens placed on the external surface of the cornea to shape the ocular material.
Figure 8:
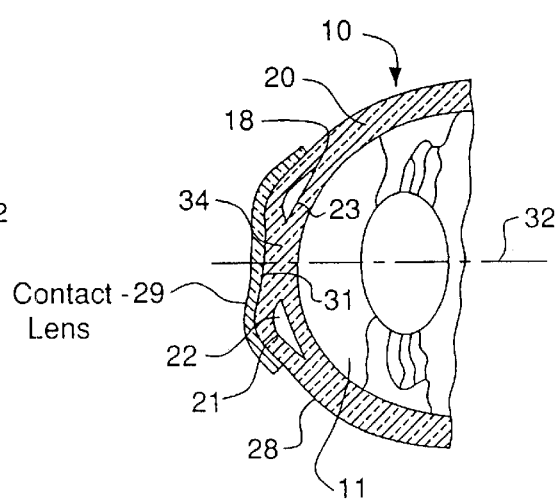
FIG. 8 is a cross-sectional side view of a eye having a ring-shaped pocket formed in between layers of the cornea with a contact lens placed on the external surface of the cornea to shape the ocular material.

As seen in FIGS. 7 and 8, when ocular material is injected or placed into pocket 18, an external contact lens 29 can be placed on the external surface of the cornea, which would allow the gel to be shaped or redistributed and, thus, the cornea to be reshaped in any manner desired. The proper size and shape of the contact lens 29 is determined by the information received from the wavefront technology. Lens 29 is preferably a temporary lens that would allow light if the visible spectrum to pass therethrough. The contact lens back surface 31 forces the gel to distribute evenly until the topographically desired configuration is achieved. Additionally, the opening 38 may allow a small amount of gel to escape, if needed, to adjust the shape and size of the ocular material 22. Wave front technology can then be used to determine if the desired correction has been achieved, and if it has not the gel can be removed via an incision and the process repeated at a later time.

Once the ocular material is in place, the patient's eye can be monitored or measured and a laser, probe 31 or other heating device can be used to reduce the overall thickness of the ocular material 22, if necessary. For instance, the ocular material 22 can initially be about 500 microns thick for ease of handling. Then, once the material 22 is positioned in the pocket 18 of the cornea, in the manner described above, the probe 40 (i.e., infrared light) can be directed to material 22 so as to reduce the overall thickness of material 22, as desired. Hence, a 500 micron thick portion of the material can be reduced, for example, to about 100 microns or any suitable thickness by the heating device. It is noted that when the pulsed laser light is focused properly to a location within ocular material 22, it can disrupt and thus shrink or melt ocular material 22 without the need of an absorbent dye. An example of such a laser is an ultrashort pulse laser, which emits nano-second pulses, pico-second pulses or femto-second pulses of laser light. Furthermore, laser light having a wavelength that is absorbed by water, or other types of energy such as microwave radiation, radio frequency radiation, or thermal energy, can be used to cause shrinkage in the lens.

Figure 21:
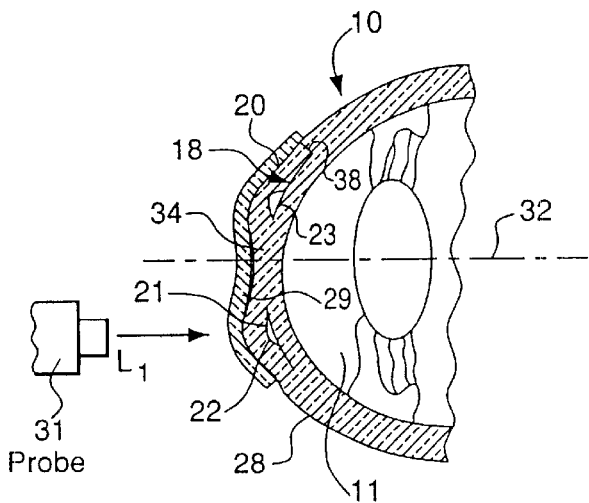
FIG. 21 is a side elevational view in cross section of a probe irradiating a portion of the ocular material to reduce the volume of the portion.

As shown in FIG. 21, an area of the material is irradiated with energy $L_1$, such as infrared light, laser light, microwave energy, radio frequency energy, or heat applied by a probe or laser 31, to cause the area of the lens to shrink or, in other words, reduce in volume. This shrinkage occurs without damage to the ocular material or other portion of the cornea 20. Accordingly, the shrinkage causes a change in the shape of the ocular material area, and thus changes the refractive power of the cornea 20 to further correct for the remaining vision disorder that was not fully corrected by the ocular material 22. The ocular material can be irradiated directly through the cornea or through lens 29.

Alternatively, the patient's vision can be monitored as the cornea 20 heals to determine if the size and shape of the ocular material 22 should be increased. The size or shape of the ocular material can be changed, and therefore the curvature of the cornea 20 can be changed without surgically opening the pocket 18. That is, as discussed above, the ocular material 22 can include certain monomers which, when irradiated with light within a certain wavelength range (e.g., blue or ultraviolet light), become agitated and cross-link, which causes the ocular material 22 to increase in size at the area of the irradiation.

Figure 22:
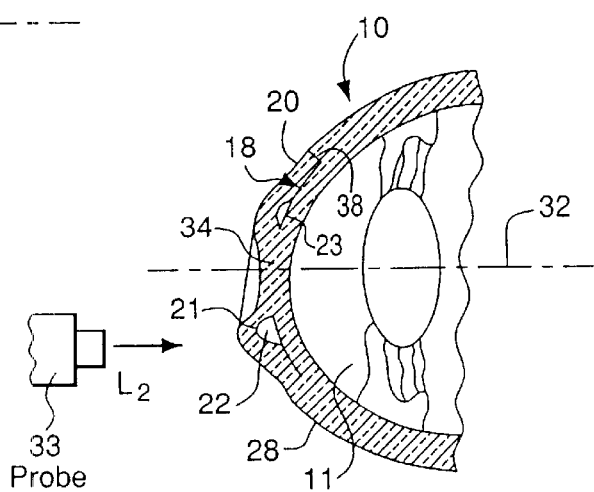
FIG. 22 is a side elevational view in cross section of a probe irradiating a portion of the ocular material to increase the volume of the portion.

As shown in FIG. 22, an area of ocular material 22 is irradiated by probe 33 or laser light $L_2$, which passes through the layer 21. The laser light $L_2$ has a wavelength, such as long ultraviolet wavelength or light within the blue light spectrum, to aggravate the monomers, which causes a cross-linking effect that increases the volume of the ocular material 22 in the area being irradiated. Hence, as the thickness of the ocular material 22 increases, this increase thickness changes the curvature of the cornea as shown, thus changing the refractive power of the cornea to a degree necessary to correct the remainder of the vision disorder that was not corrected by the insertion of the ocular material 22. The ocular material can be irradiated directly through the cornea or through lens 29.

Furthermore, a chemical can be used to polymerize or solidify the ocular material, when the ocular material is a collegen solution. Preferably, the chemical is applied to the external surface of the cornea and passes through the cornea and into the pocket 18, where it comes into contact with ocular material 22 and polymerizes the material. Preferably, the chemical used to polymerize the collegen solution is preferably about, 0.1 moler to 0.5 moler and more preferably about 0.2 moler to 0.4 moler of sodium persulphate diluted in a 0.02 moler phosphate buffer having a pH of about 8.0. However, the polymerizing chemical and the ocular material may be any suitable chemical and material known to one skilled in the art.

Furthermore, if necessary, the collegen solution can be depolymerized or returned to a gel or liquid state by applying glugaric anhydride in the same manner as described above for sodium persulphate. However, the depolymerization chemical can be any suitable chemical known in the art. Once the ocular material is depolymerized, the procedure can be repeated as often as desired. In other words, the refractive properties of the eye can be remeasured and reset and the material can be repolymerized as many times as desired until the correct refractive measurement is achieved.

To clean or wash the above chemicals from the eye, a disodium phosphate of about 0.02 molar and pH of 8.5 can be applied to the surface of the cornea.

Once the ocular material is in place and/or cross-linked or solidified as described above, the refractive properties of the eye can be remeasured using wavefront technology, and it can be determined if any refractive error remains in the eye. Generally, the refractive error is less than ±2.0 diopters sphere or astigmatism.

Figure 23:
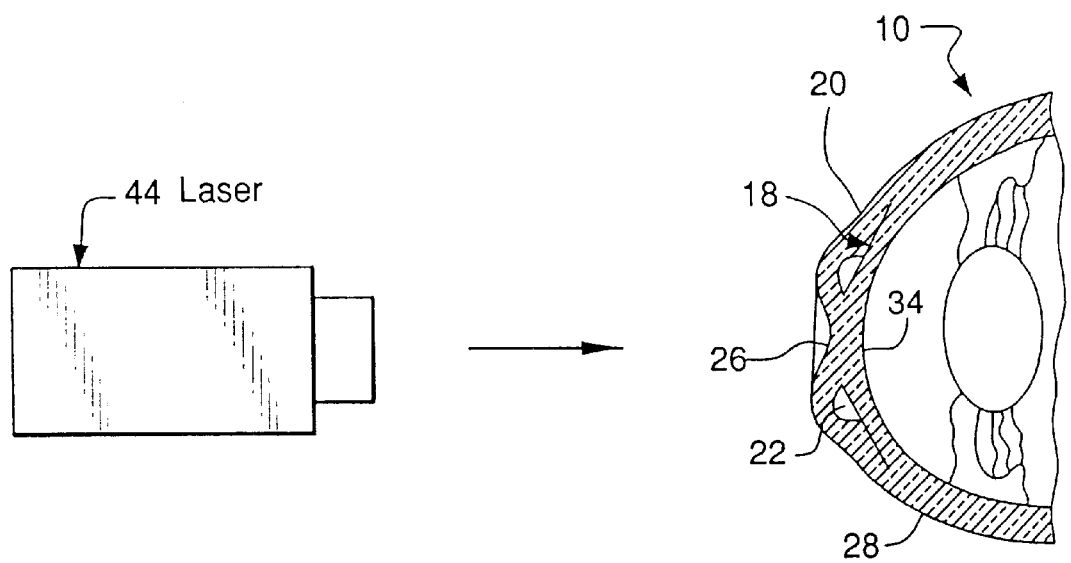
FIG. 23 is a side elevational view in cross section similar to that shown in FIG. 19, except that a portion of the external surface of the cornea has been ablated by a laser.

To reduce or eliminate this small refractive error, a second laser 44, preferably an excimer laser, can then be aimed and fired at the external surface of the cornea 24, ablating a portion 26 of the cornea, as seen in FIG. 23. Preferably, about 1–100 micron thickness is ablated, but any thickness that achieves the desired result can be ablated from the exterior surface of the cornea. The excimer laser can be applied either through the corneal epithelium or the epithelium can be reopened initially using diluted alcohol (less than 20% alcohol) or a brush. The second laser preferably ablates portion 26 of surface 22 that overlies the portion 34 attaches, but may ablate any portion desired.

Embodiment of FIGS. 25–28

In a further embodiment, a second flap 50 can be formed from the corneal epithelium on the surface 52 of the cornea 20, a seen in FIGS. 25–28 to reduce or eliminate irregularities in the healing of the cornea. Preferably, the flap is formed overlying portion 34 using a device 66 that has a sponge 68 thereon. As seen in FIG. 29, device 66 is a cylindrical tube having an opening 70 with sponge 68 inserted therein. Alcohol is fed through a hollow portion 69 that runs longitudinally along the interior of device 66. When the alcohol saturates the sponge, the sponge can be applied to the surface of the cornea. The alcohol loosens the epithelium from the basement membrane, which allows removal of the epithelial layer. If it is desired to have the flap a least partially attached as shown in FIGS. 25–28, by portion 54, a notch 72 can be formed along the edge of device 66, thereby preventing the sponge from contacting potion 54. Furthermore, the device 66 can have spikes or markers 74 at predetermined points on the edge of the device. For example, the markers can be at 90 degree or 180 degree intervals. The spikes can have a stain, such as gentian violet or any other suitable dye, applied thereto, so that the exact location and orientation of the flap is known. Therefore, when the flap is replaced or reapplied, it can be replaced in the exact or at least the substantially same position from which it was removed.

The second flap 50 is a relatively small flap that preferably at least partially overlies or is concentric about the visual axis or main optical axis 32 and can be attached to the cornea 20 by portion 54. However, the flap can be formed on any portion of the cornea desired and in any suitable manner, such as with a knife or laser. It is noted, that the location of the flap does not necessarily need to be concentric about the main optical axis and can be at any location on the surface of the eye and may be any size desired.

Figure 26:
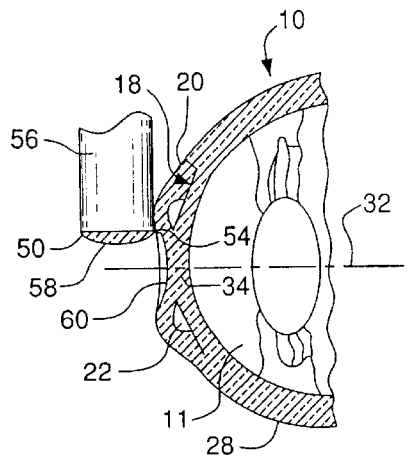
FIG. 26 is a side elevational view in cross section of the eye of FIG. 25, with the flap moved to expose an internal corneal surface.
Figure 27:
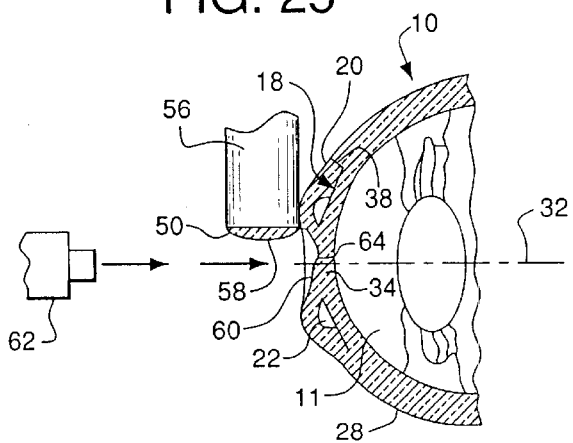
FIG. 27 a side elevational view in cross section of the eye of FIG. 26, with a laser ablating a portion of the exposed internal corneal surface.

The flap is preferably pealed or moved away from the surface of the cornea using a suction device 56 (FIG. 30), but may be removed using any other device known in the art. As seen in FIG. 30, device 56 is substantially cylindrical with air holes 57 extending through top surface 80. When suction device 56 is used, the flap is moved away from the cornea and remains attached to device 56. Generally suction is applied and air travels through passageway 82, which extends longitudinally along the interior of device 56. When surface 80 is applied to the portion of the epithelium that has had alcohol applied thereto, a vacuum is formed in passageway 82 and flap 50 can be removed, as seen in FIGS. 26 and 27, exposing third and fourth internal corneal surfaces 58 and 60. Surface 58 generally faces in a posterior direction and surface 60 generally faces in an anterior direction.

Figure 28:
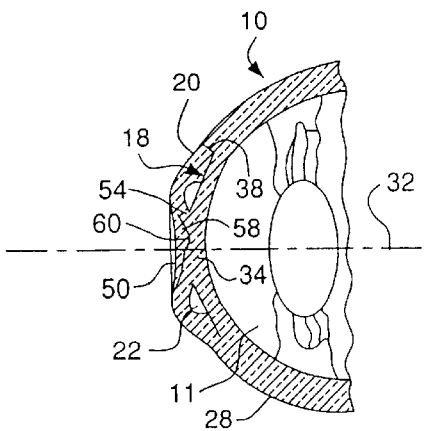
FIG. 28 is a side elevational view in cross section of the eye of FIG. 27, with the flap replaced over the ablated internal corneal surface.

Once the flap is moved to expose surfaces 58 and 60, an excimer laser 62, as seen in FIG. 27, can be used to ablate a portion 64 of the cornea 20 to reduce or eliminate any remaining refractive error. Portion 64 is preferably a portion of the Bowman's layer or basement membrane, but can be any portion of the cornea desired. The flap 50 is then replaced and allowed to heal as seen in FIG. 28. The flap may simply be placed over the ablated portion and heal or it may be affixed thereto in any manner known in the art, such as by sutures or adhesive.

When performing the excimer laser procedures described above and shown in FIGS. 23 and 27, it is possible to simultaneously use wavefront technology or Adaptec optic technology to create a near perfect correction in the eye and to remove all corneal irregularities. By using this technique to correct vision, it is possible to achieve 20/10 vision in the patient's eye or better.

The patient can undergo the second laser ablation, as seen in FIG. 23 or FIG. 27, either immediately after the insertion of the ocular implant or after a substantial time difference, such as days or weeks later, and any step or portion of the above procedure may be repeated to decrease the refractive error in the eye.

Figure 24:
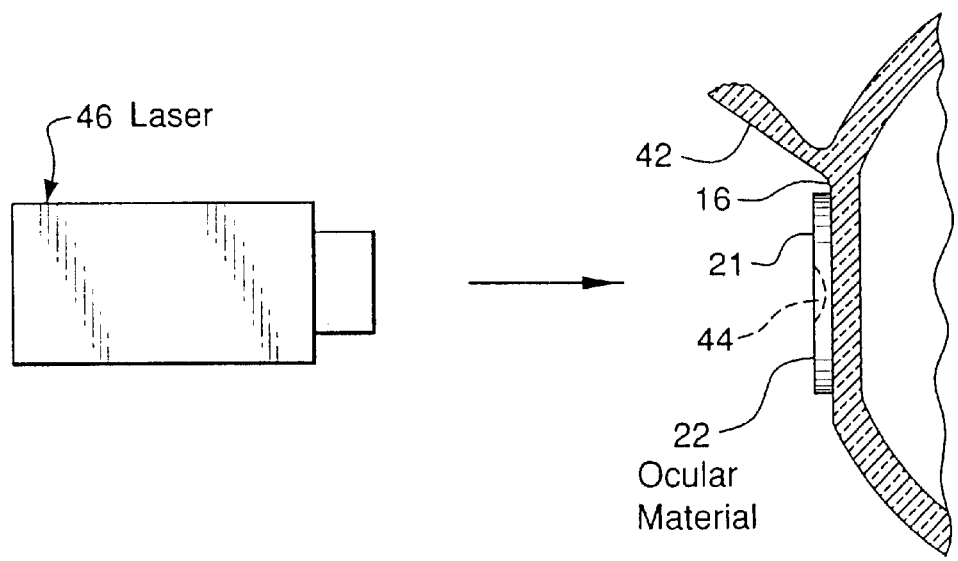
FIG. 24 is a side elevational view in cross section of the cornea with a flap formed thereon and a laser ablating a portion of the ocular material.
Figure 25:
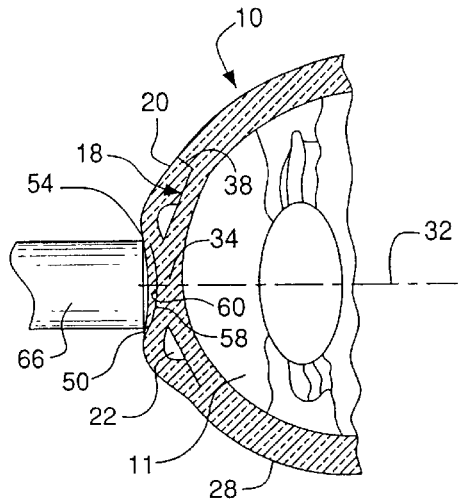
FIG. 25 is a side elevational view in cross section of an eye similar to that shown in FIG. 20, except that a flap has been formed on the surface of the cornea.

After the above procedures are preformed, and the ocular material is in place, if necessary, a flap 42 can be formed in the surface of the cornea of the eye, which would expose the ocular material 22 when removed or folded away, as seen in FIG. 24. Once the flap is removed or folded away, the ocular material can be irradiated and a portion 44 or the material 22 ablated by an excimer laser 46 and wavefront technology, as described above. Preferably, this technique is used on the pocket having no portion attached in the center, but may be used with any type of pocket, including the ring-shaped pocket.

Furthermore, at the end of the procedure or before the ablation of the surface of the cornea, topical agents, such as an anti-inflammatory, antibiotics and/or an antiproliferative agent, such as mitomycin or thiotepa, at very low concentrations can be used over the ablated area to prevent subsequent haze formation. The mitomycin concentration is preferably about 0.005–0.05% and more preferably about 0.02%. A short-term bandage contact lens may also be used to protect the cornea. The short term contact lens specifically protects the portion of the cornea that has flap 50 formed thereon, but also can protect the cornea after any of the above steps in this procedure.

While preferred embodiments have been chosen to illustrate the invention, it will be understood by those skilled in the art that various changes and modifications can be made therein without departing from the scope of the invention as defined in the appended claims.

What is claimed is:

1. A method of modifying a cornea of an eye, comprising the steps of separating an internal portion of the cornea into first and second internal corneal surfaces;

inserting ocular material in-between the first and second corneal surfaces;

forming a flap on the surface of the cornea;

moving the flap to expose a third internal corneal surface; and ablating the third corneal surface with a laser.

2. A method according to claim 1, wherein the step of forming a flap on the surface of the cornea includes forming the flap using alcohol.

3. A method according to claim 1, wherein the step of inserting ocular material includes inserting a gel in-between the first and second corneal surfaces.

4. A method according to claim 1, wherein the step of inserting ocular material includes inserting a lens in-between the first and second corneal surfaces.

5. A method according to claim 1, wherein the step of inserting a lens includes inserting a substantially ring-shaped lens.

6. A method according to claim 1, wherein the separating step includes separating an internal portion of the cornea in the stromal layer.

7. A method according to claim 1, wherein the moving step includes moving the flap using a suction device.

8. A method according to claim 1, further comprising the steps of
replacing the flap over the third internal corneal surface; and
placing a protective contact lens over the flap.

9. A method according to claim 8 wherein the step of inserting a gel in-between the first and second corneal surfaces includes inserting the gel using a needle.

10. A method according to claim 1, wherein separating the internal portion of the cornea includes separating the internal portion of the cornea so that a portion of the first surface remains attached to the second surface by an area located at the main optical axis.

11. A method according to claim 10, wherein the step of forming a flap on the surface of the cornea includes forming the flap overlying the portion of the first internal surface that remains attached to the second internal surface by the area located at the main optical axis.

12. A method according to claim 11, wherein the step of ablating the third corneal surface with a laser includes ablating a portion of the third corneal surface overlying the portion of the first internal surface that remains attached to the second internal surface by the area located at the main optical axis.

13. A method according to claim 1, wherein the step of forming a flap on the surface of the cornea includes forming the flap in the epithelial layer.

14. A method according to claim 13, wherein the separating step includes separating an internal portion of the cornea into first and second internal corneal surfaces between the external surface of the cornea and about one-third of the distance from the external surface of the cornea to an interior chamber of the eye.

15. A method according to claim 14, wherein the separating step includes separating an internal portion of the cornea using a cutting tool.

16. A method according to claim 14, wherein the separating step includes separating an internal portion of the cornea using an ultrashort pulse laser.

17. A method according to claim 16, wherein the separating step includes separating an internal portion of the cornea using an ultra short pulse laser selected from a group consisting of a femtosecond laser, a picosecond laser and an attosecond laser.

18. A method of correcting vision in an eye, the eye having a cornea and a main visual axis, comprising the steps of
forming a substantially ring-shaped pocket in the cornea of the eye adjacent to the main visual axis of the eye by separating an internal portion of the cornea into first and second substantially ring-shaped internal surfaces;
inserting ocular material in the pocket;
shaping the ocular material to a predetermined shape;
forming a flap between the external surface of the cornea and the pocket;
moving the flap to expose third and fourth internal corneal surfaces; and
ablating at least one of the third and fourth internal corneal surfaces.

19. A method according to claim 18, wherein the step of forming a flap includes forming the flap overlying the main optical axis.

20. A method according to claim 18, wherein the step of ablating at least one of the third and fourth corneal surfaces includes ablating a portion of the third corneal surface overlying the main optical axis.

21. A method according to claim 18, wherein the step of forming a flap on the surface of the cornea includes forming the flap in the epithelial layer.

22. A method according to claim 18, wherein the separating step includes separating the first and second internal corneal surfaces between the external surface of the cornea and about one-third of the distance from the external surface of the cornea to an interior chamber of the eye.

23. A method according to claim 18, wherein the separating step includes separating an internal portion of the cornea using an ultrashort pulse laser.

24. A method according to claim 23, wherein the separating step includes separating an internal portion of the cornea using an ultra short pulse laser selected from a group consisting of a femtosecond laser, a picosecond laser and an attosecond laser.

25. A method according to claim 18, wherein the step of inserting ocular material includes inserting a gel in-between the first and second corneal surfaces.

26. A method according to claim 25, wherein the step of inserting a gel in-between the first and second corneal surfaces includes inserting the gel using a needle.

27. A method according to claim 25, wherein the shaping step includes shaping the gel with a contact lens.

28. A method according to claim 25, wherein the step of forming a flap includes forming the flap using alcohol.

29. A method of correcting the refractive error in the cornea of an eye, comprising the steps of
firing a laser at the cornea of the eye to form a pocket therein, the pocket being adjacent the main optical axis;
forming an opening through the external surface of the cornea to the pocket;
inserting ocular material through the opening and into the pocket;
placing a contact on the external surface of the cornea to shape the ocular material into a predetermined configuration;

separating a layer of the cornea overlying the main optical axis to form a flap, the separated layer being in-between the external surface and the pocket;

moving the flap to expose an internal surface of the cornea that overlies the main optical axis; and ablating the exposed internal surface.

30. A method according to claim 29, wherein the step of ablating exposed internal surface includes ablating a portion of the exposed internal surface overlying the main optical axis.

31. A method according to claim 29, wherein the separating includes separating a portion of the epithelial layer to form a flap.

32. A method according to claim 29, wherein the separating step includes separating a layer of the cornea between the external surface of the cornea and about one-third of the distance from the external surface of the cornea to an interior chamber of the eye.

33. A method according to claim 29, wherein the separating step includes separating a layer of the cornea using an ultrashort pulse laser.

34. A method according to claim 33, wherein the separating step includes separating a layer of the cornea using an ultra short pulse laser selected from a group consisting of a femtosecond laser, a picosecond laser and an attosecond laser.

35. A method according to claim 29, wherein the step of inserting ocular material includes inserting a gel in the pocket.

36. A method according to claim 35, wherein the step of inserting a gel in the pocket includes inserting the gel using a needle.

* * * * *